United States Patent

Kishita et al.

[11] Patent Number: 5,202,453
[45] Date of Patent: Apr. 13, 1993

[54] FLUORINATED CYCLIC ORGANIC SILICON COMPOUNDS AND METHOD FOR MAKING

[75] Inventors: Hirofumi Kishita; Kouji Takano, both of Annaka; Koichi Yamaguchi, Takasaki; Toshio Takago, Annaka, all of Japan

[73] Assignee: Shin-Etsu Chemical Co., Ltd., Tokyo, Japan

[21] Appl. No.: 769,487

[22] Filed: Oct. 1, 1991

Related U.S. Application Data

[63] Continuation of Ser. No. 569,961, Aug. 20, 1990, abandoned.

[30] Foreign Application Priority Data

Aug. 21, 1989 [JP] Japan ................................. 1-214664

[51] Int. Cl.$^5$ .............................................. C07F 7/08
[52] U.S. Cl. .................................................. 556/448
[58] Field of Search ........................................ 556/448

[56] References Cited

U.S. PATENT DOCUMENTS

| | | | |
|---|---|---|---|
| 3,876,677 | 4/1975 | Wu | 556/448 |
| 4,898,958 | 2/1990 | Kishita et al. | 556/448 |
| 4,996,344 | 2/1991 | Inomata et al. | 556/448 |

FOREIGN PATENT DOCUMENTS

| | | | |
|---|---|---|---|
| 0328397 | 8/1989 | European Pat. Off. | 556/448 |
| 3830572 | 3/1989 | Fed. Rep. of Germany | 556/448 |

*Primary Examiner*—Paul F. Shaver

[57] ABSTRACT

Fluorinated cyclic organic silicon compounds of the general formula:

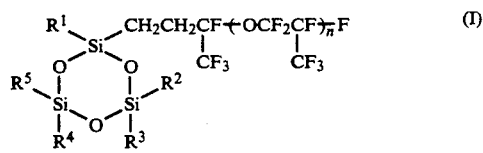

wherein $R^1$, $R^2$, $R^3$, $R^4$, and $R^5$ are independently selected from alkyl groups having 1 to 6 carbon atoms and n is an integer of from 1 to 6 are novel and susceptible to ring-opening polymerization to form chain siloxane polymers having improved properties. The cyclic compounds are produced by reacting disiloxane diols with fluorinated organic silicon compounds in the presence of amine catalysts.

10 Claims, 2 Drawing Sheets

FLUORINATED CYCLIC ORGANIC SILICON COMPOUNDS AND METHOD FOR MAKING

This application is a continuation of application Ser. No. 07/569,961 filed on Aug. 20, 1990, now abandoned.

BACKGROUND OF THE INVENTION

1. Field of the Invention

This invention relates to novel fluorinated cyclic organic silicon compounds and a method for preparing the same. The fluorinated cyclic organic silicon compounds under ring-opening polymerization in the presence of an alkaline or acid catalyst through equilibration reaction, producing chain siloxane polymers which have heat resistance, chemical resistance, water and oil repellency, and mold releasability and are useful materials for preparing silicone fluids and elastomers.

2. Description of the Prior Art

A variety of silicone fluids and elastomers are known in the prior art and have been utilized in numerous applications. There still remains a need for organic silicon compounds from which siloxane polymers having heat resistance, chemical resistance, water and oil repellency, and mold releasability can be readily produced.

SUMMARY OF THE INVENTION

The inventors have found that a novel fluorinated organic silicon compound of the general formula:

$$\text{F—(CFCF}_2\text{O)}_n\text{—CF—CH}_2\text{CH}_2\text{—Si—Cl} \quad \text{(III)}$$
$$\begin{array}{ccc} | & | & | \\ \text{CF}_3 & \text{CF}_3 & \text{Cl} \end{array} \quad \text{with } R^1 \text{ above}$$

wherein $R^1$ is an alkyl group having 1 to 6 carbon atoms and n is an integer of 1 to 6 is produced by reacting a chlorosilane of the general formula:

$$\begin{array}{c} \text{Cl} \\ | \\ \text{H—Si—R}^1 \\ | \\ \text{Cl} \end{array} \quad \text{(V)}$$

wherein $R^1$ is as defined above, with a fluorinated olefin of the general formula:

$$\text{F—(CFCF}_2\text{O)}_n\text{—CF—CH=CH}_2 \quad \text{(IV)}$$
$$\begin{array}{cc} | & | \\ \text{CF}_3 & \text{CF}_3 \end{array}$$

wherein n is as defined above, in the presence of a platinum catalyst. Further, a novel fluorinated cyclic organic silicon compound of the general formula:

$$\begin{array}{c} R^1 \diagdown \quad \diagup \text{CH}_2\text{CH}_2\text{CF}\!\!\left(\text{OCF}_2\text{CF}\right)_{\!\!n}\!\text{F} \\ \text{Si} \\ \diagup \quad \diagdown \quad | \quad | \\ O \quad \quad O \quad \text{CF}_3 \quad \text{CF}_3 \\ R^5 \diagdown | \quad | \diagup R^2 \\ \text{Si} \quad \text{Si} \\ | \diagup ^{\!\text{O}}\diagdown | \\ R^4 \quad \quad R^3 \end{array} \quad \text{(I)}$$

wherein $R^1$, $R^2$, $R^3$, $R^4$, and $R^5$ are independently selected from alkyl groups having 1 to 6 carbon atoms and n is as defined above, is produced by reacting the fluorinated organic silicon compound of formula (III) with a disiloxane diol of the general formula:

$$\begin{array}{c} R^5 \quad R^2 \\ | \quad | \\ \text{HO—Si—O—Si—OH} \\ | \quad | \\ R^4 \quad R^3 \end{array} \quad \text{(II)}$$

wherein $R^2$, $R^3$, $R^4$, and $R^5$ are as defined above, in the presence of a catalyst.

The fluorinated cyclic organic silicon compound of formula (I) readily undergoes ring-opening polymerization in the presence of an alkali or acid catalyst to produce a chain siloxane polymer which has excellent properties including heat resistance, chemical resistance, water and oil repellency, and mold releasability due to the presence of a substituent containing many fluorine atoms and is thus a useful starting material for silicone fluids and elastomers.

Briefly state, the invention provides a fluorinated cyclic organic silicon compound of formula (I) as defined above and a method for preparing the compound of formula (I) by reacting a disiloxane diol of formula (II) with a fluorinated organic silicon compound of formula (III) both as defined above.

DETAILED DESCRIPTION OF THE INVENTION

Figure 1:
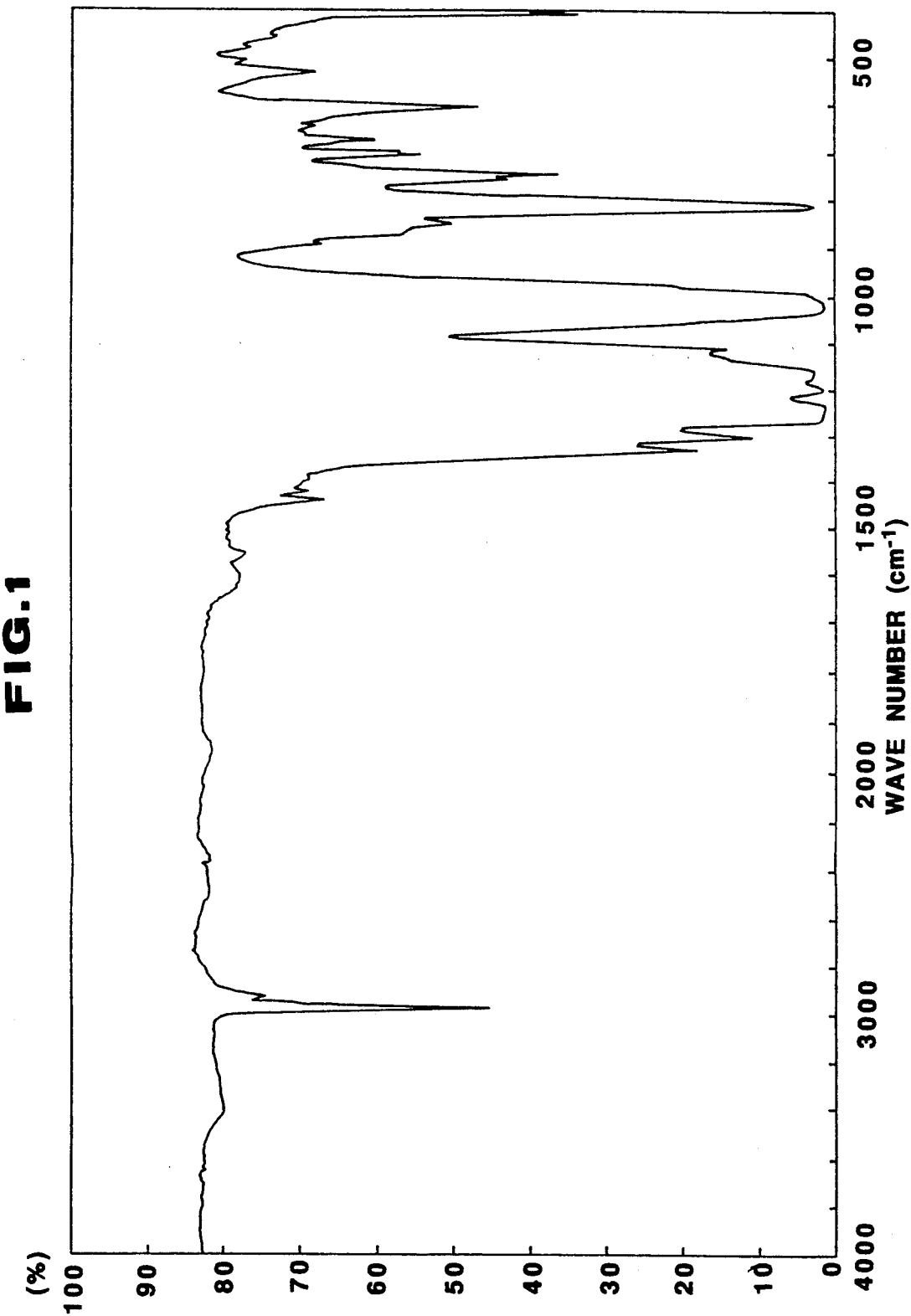
FIGS. 1 and 2 are charts showing infrared spectra of the end compounds obtained in Examples 1 and 2, respectively.

The fluorinated cyclic organic silicon compounds of the present invention are of the following general formula (I).

$$\begin{array}{c} R^1 \diagdown \quad \diagup \text{CH}_2\text{CH}_2\text{CF}\!\!\left(\text{OCF}_2\text{CF}\right)_{\!\!n}\!\text{F} \\ \text{Si} \\ \diagup \quad \diagdown \quad | \quad | \\ O \quad \quad O \quad \text{CF}_3 \quad \text{CF}_3 \\ R^5 \diagdown | \quad | \diagup R^2 \\ \text{Si} \quad \text{Si} \\ | \diagup ^{\!\text{O}}\diagdown | \\ R^4 \quad \quad R^3 \end{array} \quad \text{(I)}$$

In the formula, $R^1$, $R^2$, $R^3$, $R^4$, and $R^5$, which may be the same or different, are independently selected from alkyl groups having 1 to 6 carbon atoms, for example, such as methyl, ethyl, propyl, isopropyl and butyl groups. Letter n is an integer of from 1 to 6. With a proper choice of n to determine the size of a fluorinated substituent, the resultant siloxane polymer can have a controlled profile of properties including heat resistance, chemical resistance, weatherability, water and oil repellency, and mold releasability for a particular application.

The fluorinated cyclic organic silicon compounds of formula (I) may be synthesized by the following scheme.

(1) Oligomerization $$\text{CF}_3\text{CF}\!\!-\!\!-\!\!\text{CF}_2 \xrightarrow{\text{MF (M: K, Cs, etc.)}}_{\text{aprotic solvent}}$$
$$\diagdown \diagup$$
$$O$$

(IX)

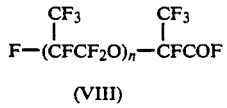

(VIII)

(2) Esterification

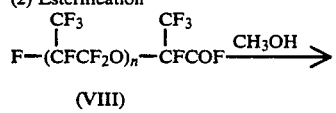

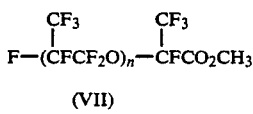

(VII)

(3) Carbinol formation

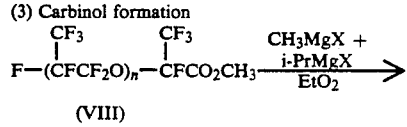

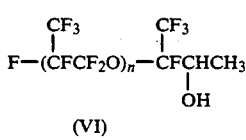

(VI)

(4) Dehydration

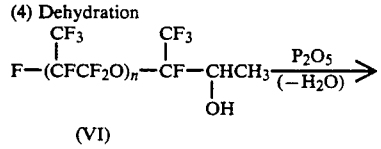

(VI)

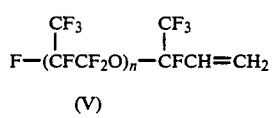

(V)

(5) Hydrosilylation

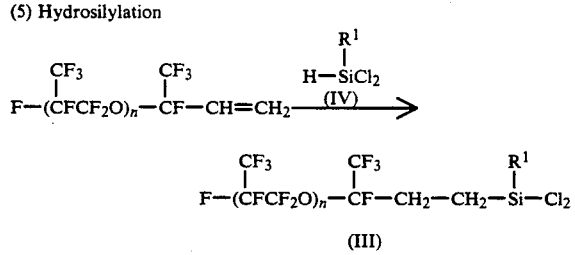

(III)

(6)

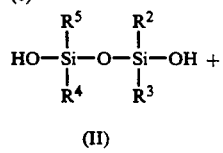

(II)

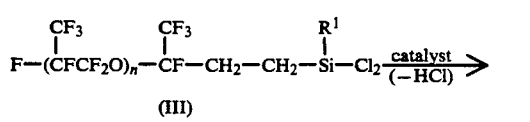

(III)

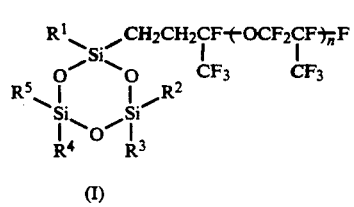

(I)

Oligomerization (1) may be carried out by an well-known method. For example, by blowing hexafluoropropenoxide (HFPO) of formula (IX) in an aprotic solvent system containing a metal fluoride such as potassium fluoride (KF), cesium fluoride (CsF) or the like at low temperatures of from $-10°$ C. to $80°$ C., there is obtained an HFPO oligomeric acid fluoride of formula (VIII). The aprotic solvents used herein include diglyme, tetraglyme, acetonitrile, and dioxane.

Esterification reaction (2) is instantaneously completed by adding dropwise the separated oligomeric acid fluoride to excess methanol with cooling at $0°$ C. to $30°$ C. Purification and isolation is done by pouring the reaction mixture into an excessively large volume of water followed by decantation, neutralization, water washing and distillation. Alternatively, each of the ester oligomers of formula (VII) may be isolated by fractionation after the HFPO oligomeric, acid fluoride is poured into excess alcohol for esterification.

Carbinol formation (3) may be effected by dissolving the ester of formula (VII) in a solvent such as ethyl ether, adding a Grignard reagent in the form of a mixture of methyl and isopropyl magnesium halides, and heating the reaction mixture. For example, an ether solution of the ester is added dropwise to a Grignard reagent at $0°$ to $5°$ C. and the reaction mixture is then stirred for one day at room temperature. The isopropyl Grignard reagent acts as a reducing agent.

Dehydration (4) is effected at a temperature of $300°$ to $400°$ C. in the presence of phosphorus pentoxide, resulting in a fluorinated olefin of formula (IV).

Hydrosilylation (5) is effected by reacting the fluorinated olefin of formula (V) with a dichlorosilane of formula (IV) in the presence of a platinum catalyst, obtaining a novel fluorinated organic silicon compound of formula (III). Preferably, the dichlorosilane and the fluorinated olefin are used in such amounts that 1 to 2 mol, more preferably 1.1 to 1.3 mol of the dichlorosilane is present per mol of the fluorinated olefin. The platinum catalyst is used in a catalytic amount which preferably ranges from $1 \times 10^{-6}$ to $1 \times 10^{-3}$ mol, especially $1 \times 10^{-5}$ to $1 \times 10^{-4}$ mol of platinum per mol of the fluorinated olefin. The typical platinum catalysts used herein are platinum group metal catalysts, for example, chloroplatinic acid, alcohol modified chloroplatinic acids as disclosed in U.S. Pat. No. 3,220,972, chloroplatinic acid-olefin complexes as disclosed in U.S. Pat. Nos. 3,159,601, 3,159,662 and 3,775,452, platinum black and palladium on alumina, silica and carbon supports, and rhodium olefin complexes. The reaction conditions may be suitably adjusted although preferred conditions include a reaction temperature of $50°$ to $150°$ C., especially $70°$ to $110°$ C. and a reaction time of about 1 to about 100 hours, especially about 5 to about 20 hours.

The final reaction (6) is effected in a solvent in the presence of a catalyst, obtaining a fluorinated cyclic organic silicon compound of formula (I). The catalysts used herein include amines such as triethylamine, pyridine, dimethylaniline and diethylamine and ureas. They are preferably used in amounts of 1 to 6 mol, especially 2 to 3 mol per mol of the fluorinated dichlorosilane. The reaction temperature preferably ranges from $0°$ to $100°$ C., especially $30°$ to $70°$ C.

The reaction may be carried out by separately preparing solutions of the compounds of formulae (II) and (III) and adding them to a solution containing the catalyst. The molar ratio of formula (II) compound to formula (III) compound preferably ranges from 2:1 to 1:2, more preferably from 1:1 to 1:1.3. The preferred solvent for the disiloxane diol of formula (II) is a polar solvent such as methyl ethyl ketone, acetone, and ethyl acetate whereas the solvent for the dichlorosilane having a fluorinated substituent of formula (III) is a fluorinated solvent such as xylene hexafluoride, perfluorooctane, and 1,1,2-trichlorotrifluoroethane.

The novel fluorinated cyclic organic silicon compounds of formula (I) are useful starting materials for preparing silicone fluids and elastomers. For instance, they are likely to undergo ring-opening polymerization in the presence of an alkali catalyst such as KOH and $(n-C_4H_9)_4POH$ or acid catalyst such as $H_2SO_4$ and $CF_3SO_3H$ by way of equilibration reaction as known for the conventional hexamethylcyclotrisiloxane, to thereby produce chain siloxane polymers. These chain siloxane polymers are useful starting materials for preparing silicone fluids and elastomers. Since the organic silicon compounds of the invention have a substituent containing many fluorine atoms in their molecule, they polymerize into siloxane polymers which not only have improved heat resistance, chemical resistance and weatherability, but also exhibit higher water and oil repellency and mold releasability than conventional ones because of reduced polymer surface energy.

There have been described novel fluorinated cyclic organic silicon compounds of formula (I) which are undergo ring-opening polymerization to produce chain siloxane polymers which have heat resistance, chemical resistance, weatherability, water and oil repellency, and mold releasability due to the presence of a fluorinated substituent and can be controlled to a desired profile of the size of a fluorinated substituent. Therefore, the fluorinated cyclic organic silicon compounds and siloxane polymers resulting therefrom are useful in preparing silicone fluids and elastomers.

EXAMPLE

Examples of the present invention are given below by way of illustration and not by way of limitation. Unless otherwise stated, parts and percents are by weight.

EXAMPLE 1

A 350-ml autoclave was charged with 105 grams of dichloromethylsilane and 36 grams of a fluorinated olefin of the following formula (Va) and further with 0.05 grams of a platinum catalyst.

$$CF_3CF_2CF_2OCFCF_2OCFCH=CH_2 \quad (Va)$$
$$\phantom{CF_3CF_2CF_2OCFCF_2OC}|\phantom{FCH=CH_2}|$$
$$\phantom{CF_3CF_2CF_2OC}CF_3\phantom{F_2OCF}CF_3$$

The autoclave was then heated to 120° C. and kept at the temperature for 50 hours for reaction. Distillation of the reaction mixture yielded 76 grams (yield 60%) of a fraction having a boiling point of 76° C./8 mmHg.

The fraction was identified to be an organic silicon compound of the following formula:

$$CF_3CF_2CF_2OCFCF_2OCFCH_2CH_2Si-CH_3 \quad (IIIa)$$
$$\phantom{CF_3CF_2CF_2OC}|\phantom{F_2OCFCH_2CH_2Si}|\phantom{CH_3}$$
$$\phantom{CF_3CF_2CF_2OC}CF_3\phantom{F_2OCF}CF_3\phantom{CH_2CH_2S}Cl$$

(with Cl substituents on Si)

through measurement of infrared (IR) absorption spectrum and nuclear magnetic resonance (NMR) spectrum as reported below.

IR spectrum:
2950 cm$^{-1}$ (C—H);
1100–1340 cm$^{-1}$ (C—F).
$^1$H-NMR spectrum:
(solvent: CCl$_4$, internal standard: CHCl$_3$)
0.9 (s, 3H, Si—CH$_3$);
1.1–1.6 (m, 2H, Si—CH$_2$—C);
2.1–2.7 (m, 2H, Si—C—CH$_2$—C).

Next, a four-necked flask having an interior volume of 2 liters was charged with 600 ml of metaxylene hexafluoride in which 44 grams of triethylamine was dissolved. The flask was equipped with two dropping funnels each having an interior volume of 500 ml. One funnel was charged with 198 grams of the fluorinated dichlorosilane of formula (IIIa) prepared above in 150 ml of metaxylene hexafluoride whereas the other funnel charged with 55 grams of a disiloxane diol of the formula:

$$\begin{array}{ccc} CH_3 & & CH_3 \\ | & & | \\ HO-Si-O-Si-OH \\ | & & | \\ CH_3 & & CH_3 \end{array} \quad (IIa)$$

in 150 ml of methyl ethyl ketone. After the triethylamine solution in the flask was heated to 50° C., the dichlorosilane and disiloxane diol solutions were added dropwise from the respective funnels at an approximately equal rate of about 1 ml/min. After dropwise addition, the reaction mixture was stirred for 30 minutes to complete reaction. The reaction product was washed with water to remove the triethylamine hydrochloride by-product and the separated organic layer was distilled in vacuum, obtaining 188 grams (yield 82%) of a fraction having a boiling point of 77° C./2 mmHg.

The compound was subjected to elemental analysis and measured for IR and NMR spectra with the following results.

| Elemental analysis: $C_{15}H_{19}O_5F_{17}Si_3$ | | | |
| --- | --- | --- | --- |
| C | H | Si | F |
| Calcd. (%) 26.24 | 2.77 | 12.24 | 47.08 |
| Found (%) 26.27 | 2.81 | 12.21 | 47.11 |

IR spectrum: see FIG. 1.
specific absorption
1020 cm$^{-1}$ (Si—O);
1000–1400 cm$^{-1}$ (C—F).
NMR spectrum: δ (ppm)
(solvent: Fron 113, internal standard: CHCl$_3$)
0.40–0.88 (m, 2H, Si—CH$_2$—C);
1.72–2.45 (m, 2H, CF—CH$_2$—C).

Based on these results, the compound was identified to be a fluorinated cyclic organic silicon compound of the following formula.

$$\begin{array}{c} C_3F_7OCFCF_2OCFCH_2CH_2\diagdown\phantom{S}\diagup CH_3 \\ \phantom{C_3F_7OC}|\phantom{F_2OC}|\phantom{CH_2CH_2}Si \\ \phantom{C_3F_7OC}CF_3\phantom{F_2}CF_3\phantom{CH_2}O\diagup\phantom{Si}\diagdown O \\ \phantom{C_3F_7OCFCF_2OCFCH}|\phantom{CH_3}\phantom{S}| \\ \phantom{C_3F_7OCFCF_2O}(CH_3)_2Si\diagdown\phantom{O}\diagup Si(CH_3)_2 \\ \phantom{C_3F_7OCFCF_2OCFCH_2CH}O \end{array} \quad (Ia)$$

EXAMPLE 2

A four-necked flask having an interior volume of 2 liters was charged with 500 ml of metaxylene hexafluoride in which 33 grams of triethylamine was dissolved. The flask was equipped with two dropping funnels each having an interior volume of 300 ml. One funnel was charged with 190 grams of a dichlorosilane having a fluorinated substituent of the formula:

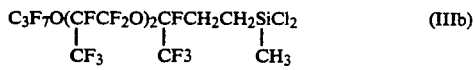

in 100 ml of metaxylene hexafluoride whereas the other funnel charged with 42 grams of the same disiloxane diol as used in Example 1 in 150 ml of methyl ethyl ketone. After the triethylamine solution in the flask was heated to 50° C., the dichlorosilane and disiloxane diol solutions were added dropwise from the respective funnels at an approximately equal rate of about 1 ml/min. After dropwise addition, the reaction mixture was stirred for 30 minutes to complete reaction. The reaction product was washed with water to remove the triethylamine hydrochloride by-product and the separated organic layer was distilled in vacuum, obtaining 268 grams (yield 86%) of a fraction having a boiling point of 110° C./3 mmHg.

The compound was subjected to elemental analysis and measured for IR and NMR spectra, with the following results.

| Elemental analysis: $C_{18}H_{19}O_6F_{23}Si_3$ | | | | |
|---|---|---|---|---|
| | C | H | Si | F |
| Calcd. (%) | 25.35 | 2.23 | 9.86 | 51.29 |
| Found (%) | 25.32 | 2.20 | 9.84 | 51.31 |

Figure 2:
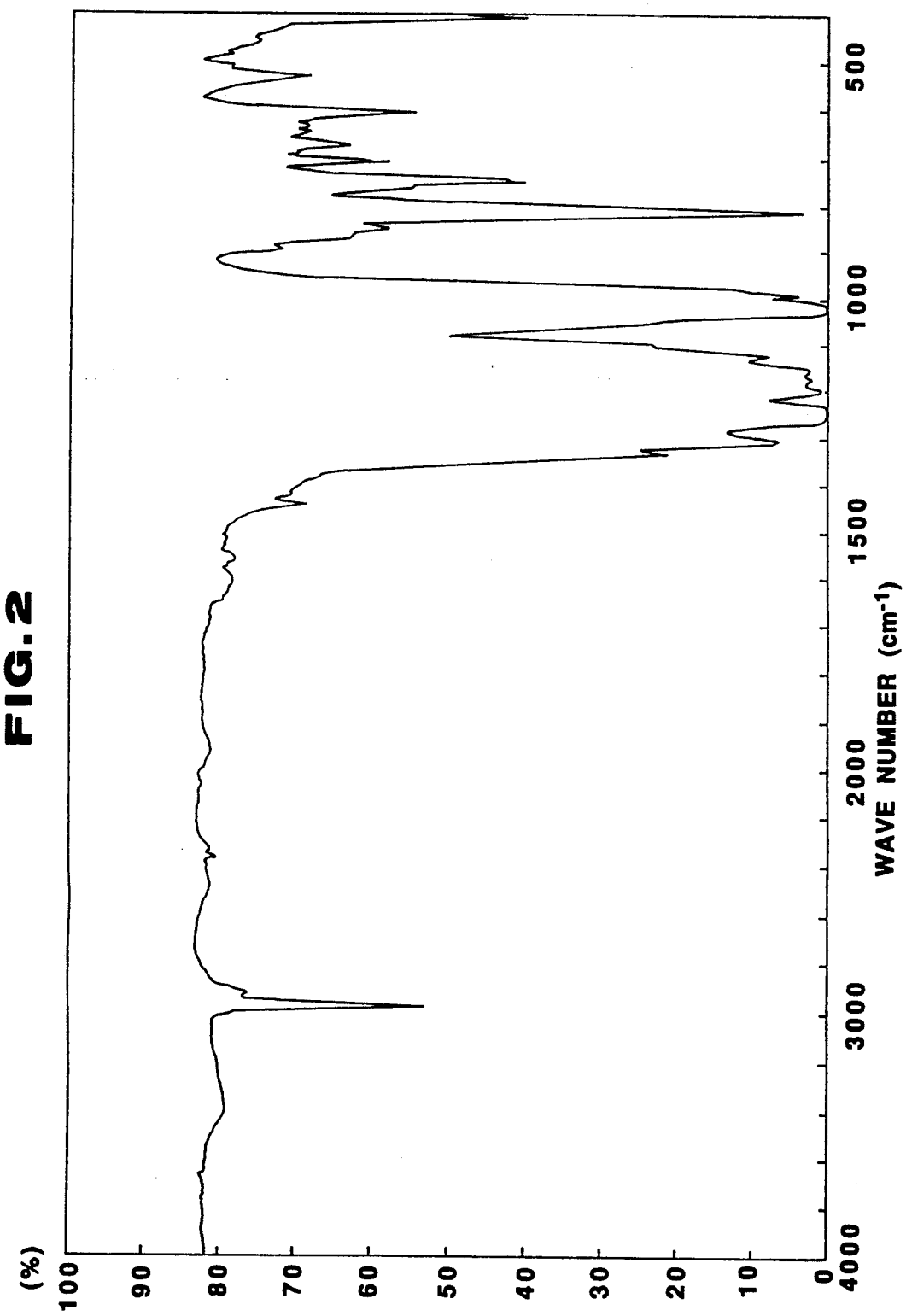

IR spectrum: see FIG. 2.
specific absorption
1020 cm$^{-1}$ (Si—O);
1000–1400 cm$^{-1}$ (C—F).
NMR spectrum: δ (ppm)
(solvent: Fron 113, internal standard: CHCl$_3$)
0.40–0.97 (m, 2H, Si—CH$_2$—C);
1.73–2.43 (m, 2H, CF—CH$_2$—C).

Based on these results, the compound was identified to be a fluorinated cyclic organic silicon compound of the following formula.

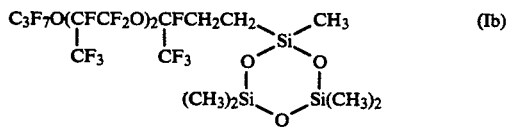

Although some preferred embodiments have been described, many modifications and variations may be made thereto in the light of the above teachings. Such variations are not to be regarded as a departure from the spirit and scope of the invention, and all such modifications as would be obvious to one skilled in the art are intended to be included within the scope of the following claims.

We claim:

1. A fluorinated cyclic organic silicon compound of the general formula:

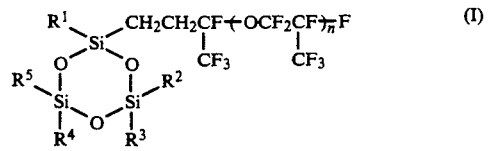

wherein $R^1$, $R^2$, $R^3$, $R^4$, and $R^5$ are independently selected from alkyl groups having 1 to 6 carbon atoms and n is an integer of from 1 to 6.

2. The fluorinated cyclic organic silicon compound of claim 1, wherein said $R^1$, $R^2$, $R^3$, $R^4$ and $R^5$ each represent the same alkyl group.

3. The fluorinated cyclic organ silicon compound of claim 2, wherein said $R^1$, $R^2$, $R^3$, $R^4$ and $R^5$ each represent a methyl group.

4. The fluorinated cyclic organic silicon compound of claim 1 wherein n is 2.

5. The fluorinated cyclic organic silicon compound of claim 2, wherein n is 2.

6. The fluorinated cyclic organic silicon compound of claim 3, wherein n is 2.

7. The fluorinated cyclic organic silicon compound of claim 1 wherein n is 3.

8. The fluorinated cyclic organic silicon compound of claim 2, wherein n is 3.

9. The fluorinated cyclic organic silicon compound of claim 3, wherein n is 3.

10. The fluorinated cyclic organic silicon compound of claim 1, wherein said compound is produced by a method which comprises reacting a disiloxane diol of the general formula (II):

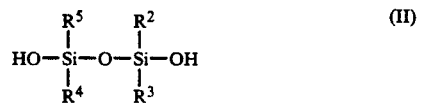

wherein $R^2$, $R^3$, $R^4$, and $R^5$ are as defined above with a fluorinated organic silicon compound of the general formula:

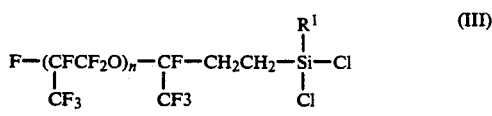

wherein $R^1$ and n are as defined above in the presence of a catalyst;
wherein said fluorinated organic silicon compound of the general formula III is prepared by a method which comprises:
  (1) subjecting hexafluoropropyloxide to oligomerization in the presence of an aprotic solvent and a metal fluoride;
  (2) esterifying the oligomer product of step (1) by reacting said oligomer product of step (1) with methanol;
  (3) subjecting the ester product of step (2) to carbinol formation by combining said ester product with methyl magnesium halide and isopropyl magnesium halide;
  (4) dehydrating the reaction product of step (3) in the presence of phosphorus pentoxide; and (5) hydrosilylating the dehydration product of step (4) by reacting said dehydration product with a dichlorosilane of the formula (IV):

$$\begin{array}{c} R^1 \\ | \\ H-SiCl_2 \end{array} \quad (IV)$$

in the presence of a platinum group metal catalyst to thereby form said fluorinated organic silicon compound of general formula III.

* * * * *